US00PP25778P2

(12) United States Plant Patent
Hurd

(10) Patent No.: US PP25,778 P2
(45) Date of Patent: Aug. 4, 2015

(54) ***PHLOX PANICULATA* PLANT NAMED 'GLAMOUR GIRL'**

(50) Latin Name: *Phlox paniculata*
Varietal Denomination: Glamour Girl

(71) Applicant: Kevin A. Hurd, Merrillville, IN (US)

(72) Inventor: Kevin A. Hurd, Merrillville, IN (US)

(73) Assignee: Walters Gardens Inc., Zeeland, MI (US)

( * ) Notice: Subject to any disclaimer, the term of this patent is extended or adjusted under 35 U.S.C. 154(b) by 89 days.

(21) Appl. No.: 13/998,834

(22) Filed: Dec. 13, 2013

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A new and unique plant cultivar of Tall Garden *Phlox, Phlox paniculata*, named 'Glamour Girl' that has powdery mildew resistant leaves, sweet-smelling, densely packed, hot-coral-pink flowers on broad strong panicles, especially suitable in the garden as a specimen or en masse, potted plant or patio, for color, fragrance and attracting hummingbirds and butterflies, and for cut flower arrangements.

1 Drawing Sheet

Botanical classification: *Phlox paniculata.*
Variety denomination: 'Glamour Girl'.

BACKGROUND OF THE NEW PLANT

The present invention comprises a new and distinct variety of Tall Garden *Phlox* botanically known as *Phlox paniculata*, and hereinafter referred to by the cultivar name 'Glamour Girl'. The new variety originated from a crossing made by the inventor, Kevin A. Hurd on Jun. 26, 2007 at a nursery in Zeeland, Mich., USA between the female parent *Phlox paniculata* 'Junior Bouquet' U.S. Plant Pat. No. 16,865 and the male parent 'Wendy House' U.S. Plant Pat. No. 18,158 with seed harvested Sep. 5, 2007. The new plant originally was designated under the breeder code 07-23-01 with final evaluations approved in the summer of 2012.

*Phlox paniculata* 'Glamour Girl' has been asexually propagated by stem cuttings at the same nursery in Zeeland, Mich. The unique characteristics of the new plant have been found to be reproducible and stable in successive generations of asexual propagation and the resultant plants have been found to be identical to the original selection. The present invention has been found to retain its distinctive characteristics through successive asexual propagations via vegetative cuttings.

SUMMARY OF THE INVENTION

*Phlox paniculata* 'Glamour Girl' is unique from all other Tall Garden *Phlox* known to the inventor. The closest comparison varieties are *Phlox* 'Junior Bouquet' U.S. Plant Pat. No. 16,865, 'Wendy House' U.S. Plant Pat. No. 18,158 and 'Junior Dance' U.S. Plant Pat. No. 16,059. 'Glamour Girl' is similar to 'Wendy House' in its upright, compact and freely basal branching plant habit but the new plant has hot coral pink rather than dark purple-colored flowers. In comparison to 'Junior Bouquet' and 'Junior Dream', the former has flowers that are a much lighter pink, and the latter has flowers that are more salmon and not as deeply colored as the instant plant. The new plant 'Glamour Girl' differs from these cultivars and all other Tall Garden *Phlox* known to the inventor in the following repeatedly observed traits in combination:

1. Bright-green, powdery mildew-resistant foliage on tall stems 45 to 50 cm tall.
2. Large flowers of hot coral-pink with darker eye on large, strong, upright, dense panicles.
3. Hardy vigorous growth habit.

BRIEF DESCRIPTION OF THE DRAWINGS

The photographs of the new plant demonstrate the unique traits of *Phlox* 'Glamour Girl' and the overall appearance of the plant at two-years old. The colors are as accurate as reasonably possible with color reproductions. Variation in ambient light spectrum, source and direction may cause the appearance of minor variation in color.

FIG. 1 shows the new plant growing in an outdoor full-sun trial bed in mid-flowering season with clean, disease-free foliage.

DETAILED BOTANICAL DESCRIPTION

The following descriptions and color references are based on the 2001 edition of The Royal Horticultural Society Colour Chart except where common dictionary terms are used. *Phlox paniculata* 'Glamour Girl' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun trial garden of a wholesale nursery in Zeeland, Mich. with supplemental fertilizer and water as needed and also a partially shaded greenhouse for color comparison, in particular of the flower.

Parentage: Female or seed parent *Phlox paniculata* 'Junior Bouquet' U.S. Plant Pat. No. 16,865; male or pollen parent *Phlox paniculata* 'Wendy House' U.S. Plant Pat. No. 18,158.

Plant habit: Vigorous; upright, bushy with multiple stems.

Plant size: 70.0 cm to 80.0 cm tall; 50.0 to 62.0 cm across at widest point (about mid flower height).

Propagation: Stem cuttings.

Time to produce rooted shoots: About 3 weeks.

Time to produce flowering plant: About 4 months during spring and summer season.

Root description: Fibrous, to about 2.0 mm diameter; root color nearest RHS 158A depending on soil type.

Branches: Glabrous; three to nine per stem without pinching; dimension about 3.0 to 10.0 cm long and to 2.0 mm diameter.

Stems: Rounded in cross section; glabrous; size about 60.0 to 72.0 cm long and 8.0 mm in diameter at base.

Stem color: Upper portion in more light nearest RHS 187B, lower portion and more shaded areas between RHS 144C and RHS N144B; stem color at node usually with dark band nearest RHS 187B.

Internode: About 15 before flower branches and 10 with flower branches; average internode length about 2.7 cm.

Leaves: Simple, opposite, oblong elliptic, with acute apex and attenuate base; leaf margin entire; adaxial and abaxial surfaces glabrous; adaxial glossy, abaxial matte; size about 12.0 cm long and 3.0 cm wide distally smaller; number of leaves per flowering stem about 32.

Leaf color: Adaxial surface between RHS 141B and RHS 143B; abaxial surface between RHS 138B and RHS 143C.

Leaf veins: Pinnate.

Vein color: Adaxial between RHS 145D and RHS 144D near base of main vein and darkening to between RHS 141B and RHS 143B distally and in secondary veins, abaxial main vein color between RHS 145D and RHS 144D with secondary veins between RHS 138B and RHS 143C.

Flower shape: Salverform; with tube about 2.2 cm long and five flared petals forming a flattened face to about 3.5 cm diameter.

Flower fragrance: Sweet.

Petal: Five, complete; smooth and glabrous both adaxial and abaxial; joined together at base to form a single corolla tube and flattened overlapping blades in face; tube dimensions about 2.4 cm long and 3.0 mm diameter; dimension of blade portion about 1.4 cm from tube to apex and 9.0 mm across.

Petal color front from outer margin toward center: Margin between RHS 51A and RHS 51B; middle lighter than RHS N155 C; thin about 1.0 mm irregular band nearest RHS 77B; center eye more yellow than RHS 192C; inside tube outer portion nearest RHS 186C; glabrous inside except densely pubescent band of about 2.5 mm wide and 3.0 mm from base inside with white RHS 155D; inside of tube base portion between RHS 145B and RHS 145C; petal face lightens to nearest RHS 54A before dropping.

Petal color back starting from outside toward center: Nearest RHS 55B; slightly lighter patches near center of petal back nearest RHS 155C; margin (less than 0.5 mm) of petal in center of inflorescence nearest RHS 70A; tube pubescent on outside; distal portion of tube with stripes of between RHS 63B and RHS 63C and nearest RHS 194C; base of tube nearest RHS 145D.

Sepals: Normally five; about 11.0 mm long and individually about 1.5 mm wide before being fused in basal 6.5 mm; sharply acute apex and fused base.

Sepal color: Adaxial nearest RHS 137A at apex and lightening to nearest RHS 138B at base with a 1.0 mm transparent margin of lighter than RHS 138D in the middle portion where fused; abaxial color nearest RHS 138B at base and RHS 138D at apex with the middle portion where fused lighter than RHS 138D.

Stamens: Five.

Filament: Fused to inside of corolla tube; about 1.0 mm long and less than 0.5 mm diameter; color lighter than RHS 65D.

Anther: Oblong; about 1.0 mm long and 0.5 mm diameter; color lighter than RHS 161D.

Pollen: Abundant, globose; color nearest RHS 18D.

Style: About 20 mm long and less than 0.5 mm diameter; color nearest RHS 72B lightening to nearest RHS 145D at base.

Stigma: Split in three in the terminal 3.0 mm; color nearest RHS 18C.

Ovary: Ovoid; about 2.5 mm long and 1.0 mm wide tapering to diameter of style in distal portion; color between RHS 141B and RHS 141C.

Peduncle: Stiff, strong, cylindrical, glabrous; flowering portion about 18 cm long and 4.0 mm diameter at base.

Peduncle color: Nearest RHS 187A in upper region with more light and between RHS 152 D and RHS 146 with tinting of nearest RHS 187C in lower region with less direct light.

Pedicel: Glaucous, stiff, strong, erect, rounded to about 0.5 cm diameter and to 1.5 cm long.

Pedicel color: Nearest RHS 187B.

Fruit: Rare, up to four seeds per longitudinally dehiscent capsule; ovoid; about 1.0 cm long and 6.0 mm diameter; mucronate with apical mucro about 2.0 mm long and 0.5 mm diameter; color at dehiscence nearest RHS 161D.

Seeds: Rare, flattened ovoid, about 4.0 mm long, 2.6 mm across and 1.5 mm thick; color variable, nearest RHS 202A, RHS 199D and between RHS 202A and RHS 202B.

Disease resistance: Plant shows resistance to powdery mildew, a disease common to many tall garden *Phlox*; other disease or pest resistance beyond that which is common to perennial, hardy, tall *Phlox* has not been noted.

Hardiness and culture: The new plant grows best with plenty of moisture and adequate drainage; hardy to at least from USDA zone 4 through 8. *Phlox* 'Glamour Girl' adds beauty and fragrance to the garden and attracts butterflies and hummingbirds.

Disease and pest resistance: *Phlox* 'Glamour Girl' demonstrated the similar excellent powdery mildew resistance of the parents under conditions that would show symptoms among all but the most resistant varieties.

I claim:

1. A new and distinct plant of Tall Garden *Phlox, Phlox paniculata* 'Glamour Girl', as herein described and illustrated.

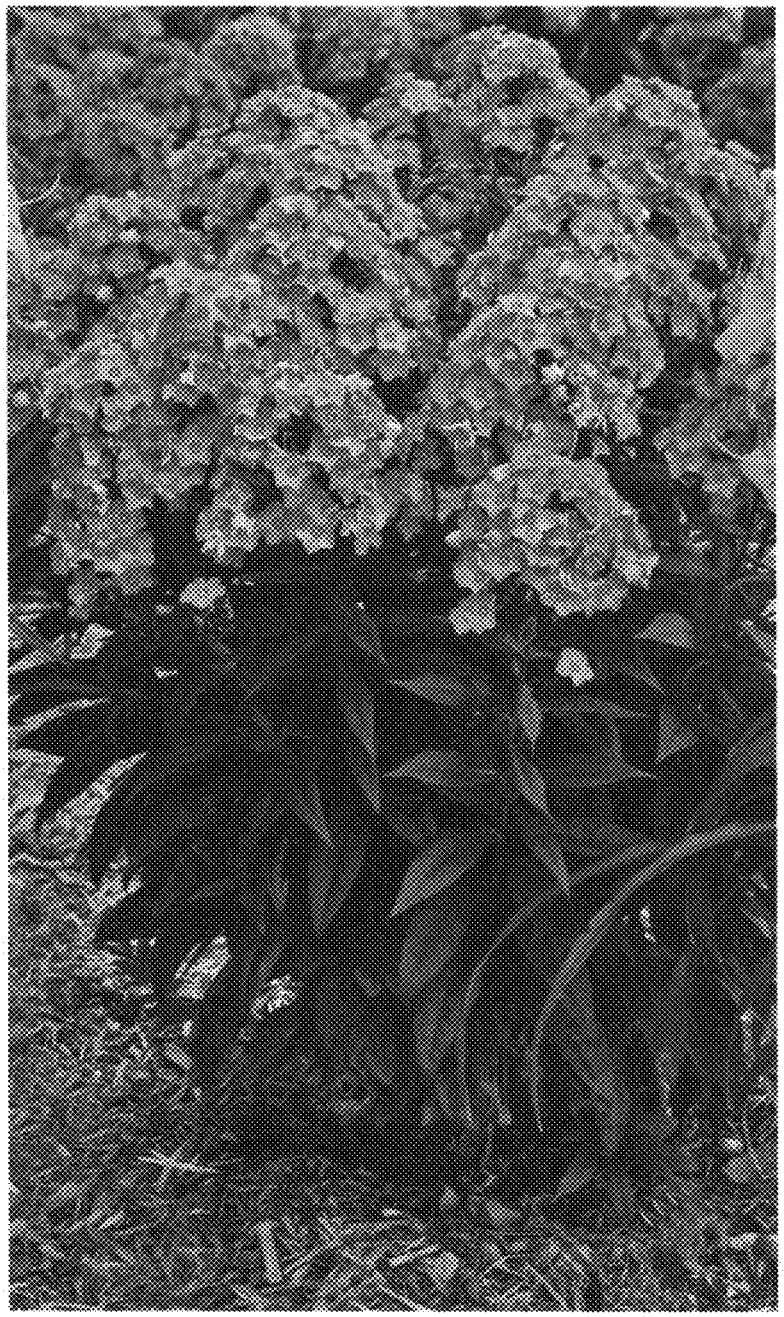

* * * * *